(12) United States Patent
Brocia

(10) Patent No.: US 6,974,676 B1
(45) Date of Patent: *Dec. 13, 2005

(54) ASSAY METHODS FOR TRANSFER PROTEINS THAT NORMALIZE FOR ACCEPTOR CONCENTRATION

(75) Inventor: Robert W Brocia, Bronxville, NY (US)

(73) Assignee: Roar Holding, LLC, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/005,711

(22) Filed: Jan. 12, 1998

(51) Int. Cl.$^7$ ............................................... C12Q 1/48
(52) U.S. Cl. ........................ 435/15; 435/11; 435/7.72; 435/7.9
(58) Field of Search ........................ 435/4, 11, 19, 7.9, 435/15, 7.72

(56) References Cited

U.S. PATENT DOCUMENTS

| | | | |
|---|---|---|---|
| 5,459,567 A | * 10/1995 | Brocia | 356/318 |
| 5,565,328 A | 10/1996 | Bascomb et al. | 435/25 |
| 5,580,747 A | * 12/1996 | Shultz et al. | 435/24 |
| 5,585,235 A | * 12/1996 | Brocia | 435/4 |
| 5,618,683 A | * 4/1997 | Brocia et al. | 435/11 |
| 5,770,355 A | * 6/1998 | Brocia | 435/4 |
| 5,846,720 A | * 12/1998 | Foulkes et al. | 435/4 |
| 6,172,750 B1 | 1/2001 | Brocia | 365/318 |
| 6,174,693 B1 | 1/2001 | Brocia | 435/7.4 |

OTHER PUBLICATIONS

U.S. Appl. No. 08/496,806, filed Jun. 29, 1995, Brocia.

* cited by examiner

Primary Examiner—Ralph Gitomer
(74) Attorney, Agent, or Firm—Morrison & Foerster LLP

(57) ABSTRACT

A method to measure protein wherein said method internally controls for factors that affects protein activity such as substrate concentration.

6 Claims, 3 Drawing Sheets form products X and Y may be
ASSAY METHODS FOR TRANSFER PROTEINS THAT NORMALIZE FOR ACCEPTOR CONCENTRATION

FIELD OF THE INVENTION

This invention relates generally to the field of biochemistry and clinical chemistry. More particularly, the invention is a novel method to measure the activity of an enzyme.

BACKGROUND OF THE INVENTION

Conventional characterization of a protein with enzymatic activity is expressed in terms of product formed per mass of protein present per unit time. This is referred to as the specific activity of the protein. For example, a protein that hydrolyzes a substrate to form products X and Y may be described as having a specific activity of moles of X or Y formed per gram of protein per minute This specific activity determination requires two separate laboratory procedures 1) a measurement of the amount of product formed (moles) in a certain amount of time by a sample of the protein, and 2) an assay to determine the protein mass (gms) present in the sample. Normally the protein mass is measured in a colorimetric assay such as a Lowry protein assay or a BCA assay. The mass determination requires that a portion of the protein be sacrificed so that it may be reacted with the Lowry reagents.

The conventional specific activity characterization is limited to proteins that have bond breaking and/or making activity such as lipases, esterases, oxidases and others. The bond breaking and/or making activity is defined herein for ease of explanation of the invention as activity that makes and/or breaks chemical bonds.

For example, cholesterol ester transfer protein (CETP) is a plasma protein that shuttles lipids among lipoproteins which includes high density lipoprotein (HDL), low density lipoprotein (LDL) intermediate density lipoprotein (IDL), very low density lipoprotein (VLDL) and chylomicrons. If the plasma CETP activity is measured in a group of patients, the measurement must take into account the concentration of lipoprotein particles present in each sample. This is conventionally achieved by adding an excess of VLDL or LDL to the test sample to normalize the acceptor concentration among each sample. The conventional CETP assay would include a volume of a patient's plasma combined with a CETP compatible cholesteryl ester (CE) donor particle. The CE is labeled so that the CE mass may be quantitated after the protein shuttles the CE from donor to acceptor. A suitable acceptor is added to the plasma and donor mixture in a buffer to replicate physiological conditions. The donor, acceptor, plasma and buffer mixture is incubated. After incubation, the assay is analyzed to determine the amount of labeled CE transferred from donor to acceptor.

The added acceptor is in excess and compensates for the differences in lipoprotein particle numbers associated with each patient's plasma lipoprotein profile. If the acceptor were not added, the endogenous lipoproteins would accept the transferred CE and results of the test would vary based not only upon activity of the protein but also according to teach patient's lipoprotein profile.

OBJECTS AND ADVANTAGES

Accordingly, several objects and advantages of the invention are an enzyme assay that internally controls the assay result for factors that affect enzyme activity.

It is also a principal object of the invention to characterize a protein activity in one assay. It is another object of the invention to characterize a protein activity in a clinical sample for the purpose of diagnosis of a disease.

Still further objects and advantages will become apparent from a consideration of the ensuing description and accompanying drawings.

SUMMARY OF THE INVENTION

The present invention is a method to measure protein wherein said method internally controls for factors that affects protein activity such as substrate concentration.

The present invention is useful for characterization of these proteins and other proteins that do not make and/or break bonds. For example, proteins such as cholesteryl ester transfer protein (CETP), microsomal triglyceride transfer protein (MTP), phospholipid transfer protein (PLTP) do not cleave a chemical bond. These proteins express their activity by transporting lipids among donor/acceptor sites, it is believed that the activity of these proteins is modulated according to the liquid crystalline states of their respective substrates and may follow an entropy gradient and in addition there are proteins that do make/break bonds but are unusual in that there activity changes according to the physical state of the substrate, i.e. lipase. All these lipid active proteins CETP, MTP, PLTP and lipase and others including lecithin cholesterol acyl transferase (LCAT), ACAT and others including enzymes that react with protein substrates of varying liquid crystalline states may be characterized by the present invention.

The present invention is also useful to characterize enzymes that are described by conventional means. The present invention is utilized to characterize all enzymes and normalizes the activity of the enzyme by the amount of substrate or protein mass present. The invention accomplishes this for use such as in the clinic where samples of physiological fluids may contain protein activity. The samples may demonstrate varying protein activity from patient to patient. The differences in activity solely due to the amount of protein present in the sample of active mass must be discerned from activity due to varying amounts of substrate present in the sample.

The present invention improves upon the conventional methods of determining CETP activity in a plasma sample. The present invention eliminates the acceptor of the previous method. Thus reducing variability associated with VLDL preparations and further eliminates hazards involved with the handling of human blood products. The components of the method are more stable and have a longer shelf life without VLDL.

The present invention includes a CE donor with a fluorescent label on the CE. The fluorescent cholesteryl ester is 22-(N-7-nitrobenz-2-oxa-1,3-diazol-4-yl)amino-23,24-bis-nor-5-cholen-3-yl linoleate (NBD-CE). The CE with fluorescent label (NBD) included in the donor is formatted so as CETP activity causes a change in fluorescence over time. Furthermore, the invention includes the fluorescent label to block reaction with non-CETP proteins such as cholesteryl esterase.

DETAILED DESCRIPTION OF THE INVENTION

The present invention is a method to characterize protein activity wherein the characterization is not calculated from separately determined values such as activity and protein mass. The present invention involves an enzyme activity parameter and a normalization parameter. The activity parameter method according to the invention is a protein activity assay where in the result, i.e., net chemiluminescence or fluorescence of the activity assay will change when an assay to determine the concentration of the protein, substrates or other factor of interest in performed if the change in the result is not due to a change in protein activity.

The present invention is a clinical diagnostic test wherein the result of the test on a sample solution is obtained in one determination from one instrument yet the result that is detected by the instrument is due to a combination of more than one independent spectrophotometric assay. One spectrophotometric assay emits light and another alters the optical density of the assay. The combined effect is measured as one result by one instrument.

A clinical diagnostic test wherein the result is measured by one instrument in one determination and the result is a function or more than one chemical indicator where each chemical indicator functions independently.

The invention is a screen for inhibitors or promoters of protein activity for the purpose of pharmaceutical drug development.

This invention disclosure provides several examples of different fluorescent activity assays where the emitted light is varied according to protein activity and then adjusted with respect to the substrate concentration or, alternatively, adjusted with respect to protein concentration by immunological techniques or colorimetric assay.

The activity parameter is established with a light emitting measurement technique that includes fluorescent and chemiluminescence enzyme activity assays where the protein activity is assessed by a fluorimeter or illuminometer was a change in light emission intensity.

Figure 1:
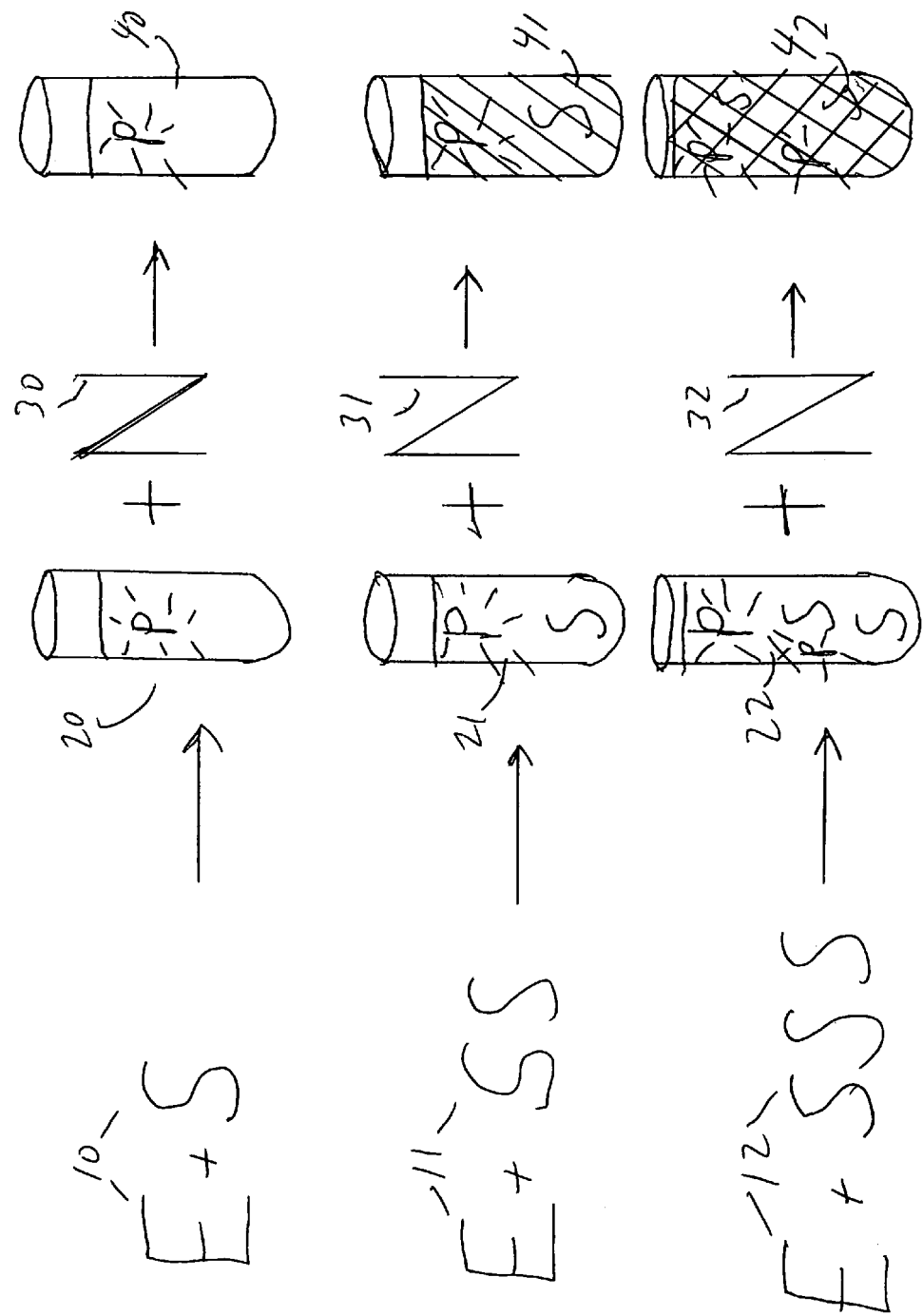
FIG. 1 is an illustration that depicts the light emitting enzyme activity determination step of the assay followed by the normalization step of the assay in three different samples.

FIG. 1 illustrates the enzyme activity dependent fluorescence or chemiluminescence portion of the method according to the invention followed by the substrate or product normalization portion of the invention. In FIG. 1, enzyme and substrate interactions 10, 11, 12 are depicted so substrate concentration is increasing from 10 to 12. After enzyme substrate interaction fluorescent or chemiluminescent products 20, 21, 22 are obtained. The products are of varying fluorescent or luminescent intensity according to varying substrate concentration. Normalization factor 30, 31, 32 is interacted with the light emitting mixture and color develops 40, 41, 42 according to the increasing substrate concentration present. The developed color causes an increasing optical density thus modulating the light emission intensity from the mixture. The fluorimeter or illuminometer or other light detecting instrument would collect the substrate dependent light emission intensity.

Figure 2:
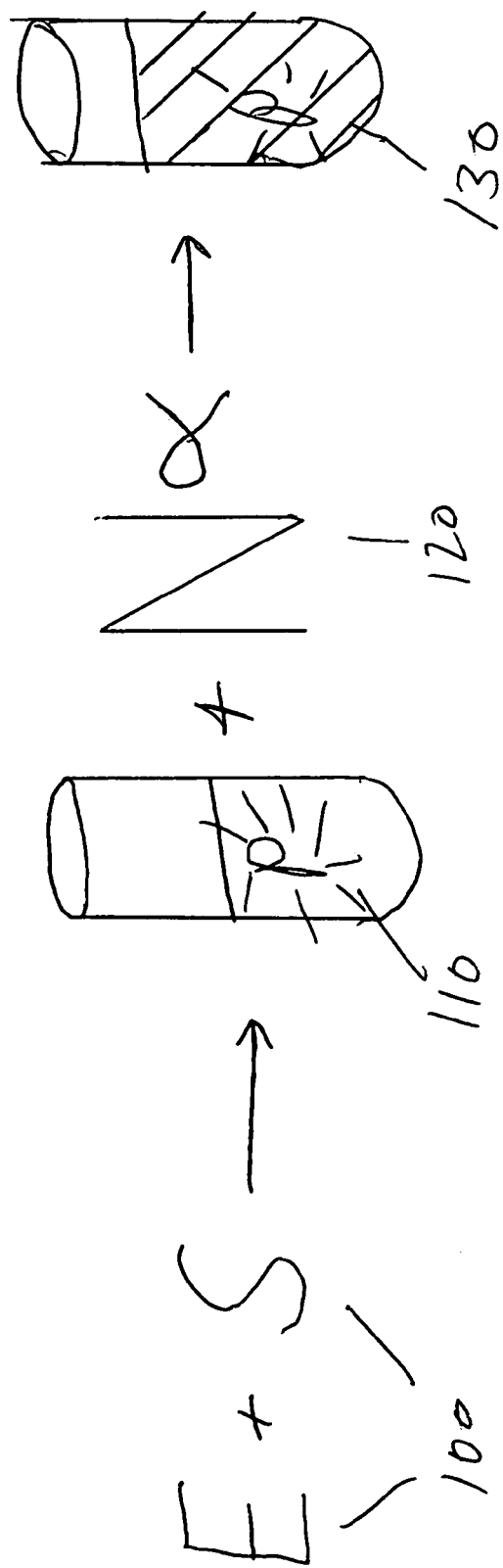
FIG. 2 shows the invention as immunoturbidometric normalization is applied.

FIG. 2 illustrates another embodiment of the invention. Enzyme and substrate mixture 100 yields an activity dependent light emitting product 110. Normalization factor 120 is an antibody specific for the enzyme and immunoprecipitation components. Resulting mixture 130 is turbidprecipitated antibody/enzyme complex and the turbidity blocks the emitted light from the light emitting product formed by the enzyme activity. The results are light emission intensity that is normalized by enzyme mass present.

EXAMPLES

The following are specific examples involving certain proteins of interest to provide a complete understanding of the invention:

In the diagnosis of heart disease the lipid transfer proteins seem to play an important role. The many complex interactions involving lipids make a clear path for intervention difficult to perceive. For example, the relationship between saturated fats in a patient's diet and the patient's total plasma cholesterol is believed to be a factor of solubility. If an amount of saturated fat is packaged in a lipoprotein particle core, the lipoprotein particle core will also solubilize cholesteryl ester. Cholesteryl ester has an increasingly limited solubility in triglycerides (TG) of increasing saturation which means a fixed mass of cholesteryl ester will require more lipoprotein particles for solubilization if the triglyceride is of a more saturated type. Fewer lipoprotein particles are required if the TG is of an unsaturated type.

Therefore, a saturated fat diet will generate more lipoprotein particles to move about an equivalent amount of cholesteryl ester. Additionally, free cholesterol will partition into the lipoprotein fraction at about 3% solubility factor from the plasma red cells boosting plasma cholesterol in a saturated fat diet dependent manner.

Cholesteryl ester transfer proteins (CETP) is a protein present in normal human plasma. CETP transfers lipids among lipoprotein particles. Of the most important of these transfer events is the transfer of cholesteryl esters (CE) from high density lipoprotein (HDL) to low density lipoprotein (LDL) or very low density lipoprotein (VLDL).

This example is important to express the invention in terms of an unusual enzyme such as CETP because with CETP a product is not formed by breaking chemical bonds as with other enzymes. Proteins such as cholesteryl ester transfer protein (CETP), microsomal [triglyceride] transfer protein (MTP), phospholipid transfer protein (PLTP) do not cleave a chemical bond. These proteins express their activity by transporting lipids among donor/acceptor sites, it is believed that the activity is according to an entropy gradient and in addition there are proteins that do make/break bonds but are unusual in that their activity also changes according to the physical state of the substrate, i.e., lipase. These lipid active proteins, CETP, MTP, PLTP and lipase and others including lecithin cholesterol acyl transferase (LCAT), acyl cholesterol acyl transferase (ACAT) and other enzymes not lipid active, including enzymes that react with protein substrates according to the liquid crystalline states of the protein substrates.

Conventionally, CETP activity cannot be expressed as a specific activity because there is no product formed by making/breaking chemical bonds. The following example presents one embodiment of the present invention as a clinical method to measure CETP activity:

A suitable volume of the patient's plasma is incubated with the CE donor in buffer according to the invention. The CE donor is comprised of a fluorescently labeled CE. The fluorescent label includes NBD. The fluorescence increases, in the case of NBD, over time as the plasma CETP transfers the fluorescent CE from the donor to endogenous lipoprotein particles.

The fluorescence intensities among the group of samples will be varied according to the CETP activity in the samples and any variability among the concentrations of lipoproteins in samples. For example, differences among a patient's LDL cholesterol will be reflected in the activity of CETP. This is explained by the LDL cholesterol values resulting from the actual number of LDL particles present in the plasma. So a patient's plasma sample that is high in LDL cholesterol has more LDL particles in suspension then a patient who has a low LDL cholesterol. The patient's plasma with high LDL cholesterol will appear to have a high CETP activity when in fact the apparently high activity is due to the greater number of LDL particles available to accept transfer of the NBD-CE or other fluorescent cholesteryl ester.

Furthermore, given two patients with identical CETP activity and lipoprotein profiles, one has a meal and the other is fasted, the CETP is measured with donor and no exogenous acceptor. The fed patient will have an apparent increase in CETP activity because of chylomicron particles that circulate in the plasma after meals as a normal component of digestion. The chylomicrons will behave as acceptor of CE. The CETP activity will appear to be higher in the fed patient when in fact CETP mass may not change.

The present invention accounts for variable lipoprotein profiles by normalizing with a color development reaction in response to cholesterol and/or triglyceride and/or phospholipid and/or protein. The development of color creates a quenching effect upon the fluorescence of the CE. Therefore, the greater the concentration of CE/TG/PL/protein the greater is the color quenching effect upon the fluorescent label. This normalizes the fluorescent intensity for LDL concentration.

The present invention provides an assay that yields one value representing the activity of an enzyme. The invention accounts for enzyme specific variables that may normally affect the activity of a protein in an activity assay.

The invention is applied to the measurement of activity of CETP present in a patient's plasma through the use of a synthetic donor particle. The donor particle provides a source of fluorescently labeled CE to the protein. The CE is present in a self-quenched state in the core of the donor particle. Therefore, when the CE is removed from the core by the protein a measurable increase in fluorescence occurs. The CETP shuttles the cholesteryl ester from the donor particle to endogenous lipoproteins present in the plasma sample. These endogenous lipoproteins act as acceptor particles. The more active the CETP the higher is the fluorescence after a period of time.

The patient's plasma will have a variable amount of endogenous lipoprotein acceptor particles dependent upon the patient's particular plasma lipoprotein profile. Therefore, the fluorescence increased from the activity of the CETP present in a patient's plasma is dependent on the concentration of lipoproteins present in their plasma as well as the activity of the CETP. The invention provides a normalization factor based upon substrates of the CETP which include endogenous cholesteryl esters and triacyl glycerols, the major core components of endogenous HDL, LDL and VLDL. The normalization factor may also include phospholipids or cholesterol or any component present in the sample that would have an effect on CETP activity.

The normalization factor includes a colorizing factor that reacts in response to the normalizing factor of choice. For example, in the case of CETP, neutral lipids (CE and/or TG) may be used as the normalizing factor. A mixture of cholesteryl esterase (CEH)>100 U/L, cholesterol oxidase (CO) 300 U/L, peroxidase (PO) 1000 U/L, 4-aminoantipyrine 0.3 mmol/L, p-hydroxybenzenesulfonate 30 mmol/L in a buffer at pH 6.5 (in the case of CE as the normalization factor) is added to the incubation comprising fluorescent CE/donor and plasma. The CEH hydrolyzes any non-fluorescent cholesteryl esters to cholesterol. The cholesterol is oxidized by CO to cholest-4-en-3-one and hydrogen peroxide. The hydrogen peroxide is coupled with 4-aminoantipyrine and p-hydroxybenzenesulfonate in the presence of PO to yield a quinoneimine dye. The assay changes color in response to the concentration of C/CE in the plasma sample [not responding to the fluorescent CE in the donor due to the fluorescent label blocking CEH binding but not CETP. The higher the concentration of the C/CE from the endogenous plasma lipoproteins, the darker the color from the colorimetric assay. Increased color decreases the measurable fluorescence intensity of the activity assay due to color quenching of the fluorescent label thereby normalizing the results according to the endogenous lipoproteins present in the plasma.

Normalization for TG in the assay includes the addition of a mixture of reagents that respond to TG with a color development. For example, a mixture of reagents that include: adenosine triphosphate (ATP) 0.3 mmol/L, magnesium salt 3 mmol/L, 4-aminoantipyrine 0.15 mmol/L, sodium N-ethyl-N-(3-sulfopropyl)-m-anisidine 1.69 mmol/L, lipase 50,000 U/L (LP), glycerol kinase 1000 U/L (GK), glycerol phosphate oxidase 2000 U/L (GPO), peroxidase (PO) and buffer at pH 7.0 is added to the assay. Triglycerides are hydrolyzed by LP to glycerol and free fatty acids. Glycerol is phosphorylated by ATP forming glycerol-1-phosphate (G-1-P) and adenosine-5-diphosphate in a reaction catalyzed by GK. G-1-P is then oxidized by GPO to dihydroxyacetone phosphate and hydrogen peroxide. A quinoneimine dye is produced by the PO catalyzed coupling of 4-aminoantipyrijne and sodium N-ethyl-N-(3-sulfopropyl)-m-anisidine with hydrogen peroxide. The color develops according to the concentration of triglyceride present in the assay. The color affects the fluorescence intensity reading determined by the instrument.

The invention internally normalizes CETP activity based upon CE or TG concentration of a patient's plasma.

It is important to note that although the normalization components of the invention are indicator enzymes which hydrolyze specific substrates present in plasma to effect a optical density change, the indicator enzymes do not react with the fluorescently labeled cholesteryl ester of the donor particle.

Figure 3:
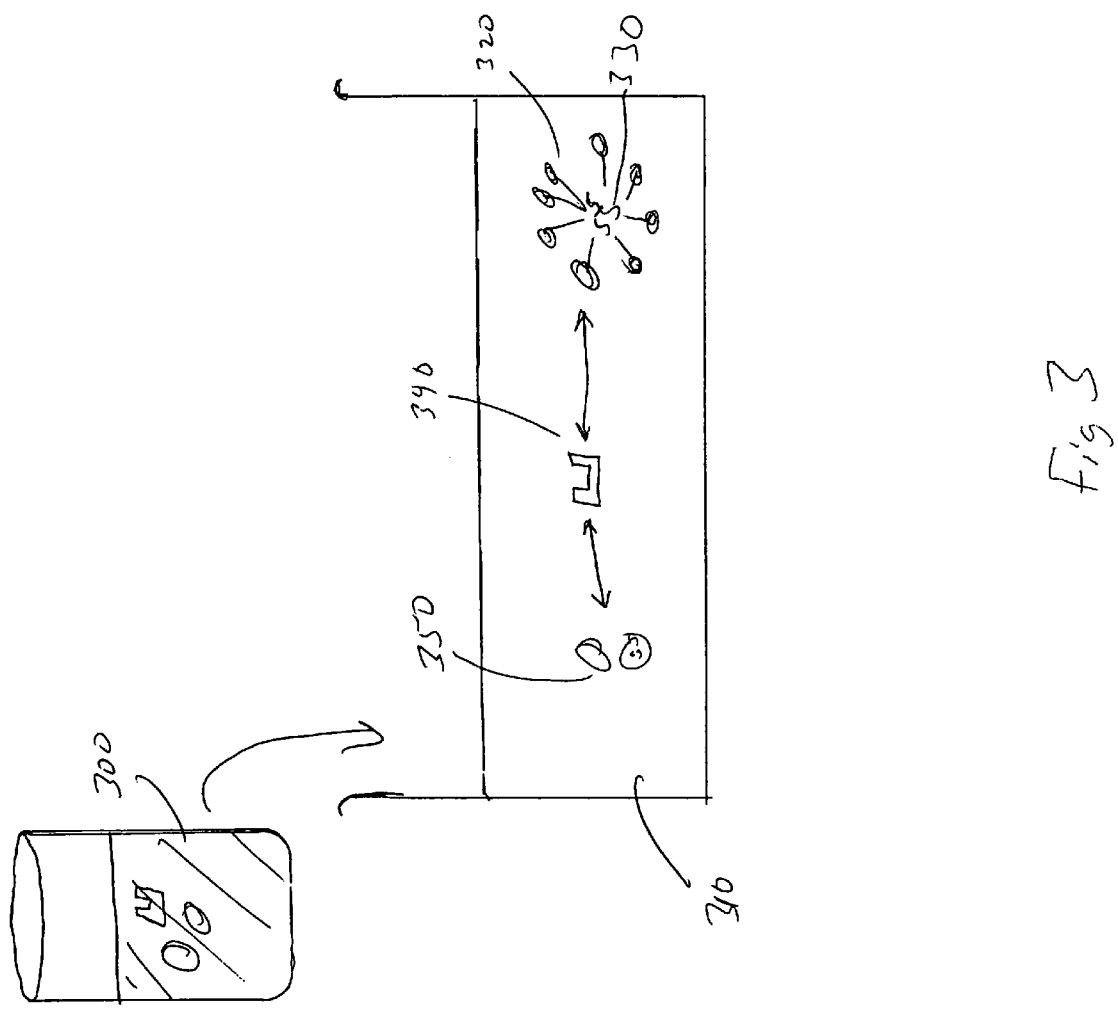
FIG. 3 shows the invention applied to lipid transfer protein, specifically CETP.

The present invention is applied to lipid transfer proteins, such as CETP according to the figures as follows: in FIG. 3, a sample 300, is a plasma or other physiological sample that may include variable concentrations of lipoproteins and CETP. A volume of the sample is incubated in an appropriate buffered incubation mixture 310 with fluorescent cholesterol ester donor particle 320 comprised of self-quenched fluorescently labeled cholesterol ester 330. During incubation CETP 340 present in the sample transfers fluorescently labeled cholesteryl ester to any acceptors 350, such as lipoproteins, present in the sample. As transfer occurs there is an increase in fluorescence intensity in the incubated sample. The increase is dependent upon the activity of lipid transfer protein and the concentration of endogenous acceptor present in the sample. The normalization factor is applied according to the invention and may include normalization with respect to the lipid transfer protein by utilizing an immunoprecipitation technique with a CETP antibody. The normalization may be based on calorimetric techniques utilizing TG and CE due to the presence of endogenous lipoproteins in the sample.

Accordingly, it can be seen that the invention provides a convenient technique to characterize a protein activity in one instrument with the inclusion of at least two spectrophotometric assays.

Although the description above contains many specificities, these should not be construed as limiting the scope of the invention but as merely providing illustrating of some of the presently preferred embodiments of this invention. Various other embodiments and ramifications are possible within its scope. For example, virtually any protein activity may be assayed with one internally controlled assay according to the invention.

Thus the scope of the invention should be determined by the appended claims and their legal equivalents, rather than by the examples given.

What is claimed is:

1. A method for determining activity of a protein lipid transferase that transports a lipid from a donor to an acceptor which method comprises:
    (a) incubating a sample containing said lipid transferase and an undetermined concentration of acceptor with
        (i) a donor particle comprising said lipid labeled with a fluorophore in a quenched state so that emitted light detectable from said labeled lipid increases when the labeled lipid is released from the donor particles and transferred to acceptor; and
        (ii) reagents that generate a color in proportion to the concentration of acceptor, wherein the color absorbs light emitted by the fluorophore; and
    (b) measuring the intensity of the detectable light, whereby the activity of the lipid transferase is determined as proportional to the intensity of the detectable light, independent of the concentration of acceptor.

2. A method for measuring activity of CETP in a sample which method comprises
    (a) incubating a sample containing CETP and an undetermined concentration of LDL and/or VLDL with
        (i) a donor particle comprising a cholesteryl ester (CE) labeled with a fluorophore in a quenched state so that the intensity of emitted light detectable from said fluorophore increases when the labeled CE is transferred to VLDL and/or LDL; and
        (ii) reagents that generate a color from cholesteryl ester (CE) or from triglyceride (TG) that is not bound to fluorophore which CE and TG are present at concentrations proportional to the concentration of VLDL and/or LDL in the sample wherein the color absorbs light emitted by the fluorophore; and
    (b) measuring the intensity of the detectable emitted light whereby the activity of the CETP in the sample is determined as proportional to the detectable emitted light, independent of the concentration of LDL and/or VLDL.

3. The method of claim 2 wherein the color is generated from cholesteryl ester or triglyceride by a method which comprises generating hydrogen peroxide.

4. The method of claim 2 wherein the fluorescent label is 7-nitrobenz-2-oxa-1,3-diazole (NBD).

5. The method of claim 2 wherein the reagents that generate a color from unlabeled CE are cholesterol esterase (CEH), cholesterol oxidase, peroxidase, 4-amino antipyrine, and p-hydroxybenzenesulfonate.

6. The method of claim 3 wherein the reagents that generate color from TG are adenosine triphosphate, magnesium salt, 4-amino antipyrine, sodium n-ethyl-n-(3-sulfopropyl)-m-anisidine, lipase, glycerol kinase, glycerol phosphate oxidase, and peroxidase.

* * * * *